United States Patent
Wuepper

(10) Patent No.: US 7,846,121 B2
(45) Date of Patent: Dec. 7, 2010

(54) DEVICE FOR EXTRACORPOREAL IRRADIATION OF A LIQUID CONTAINING BILIRUBIN, AND METHOD THEREFOR

(75) Inventor: Andreas Wuepper, Bad Homberg (DE)

(73) Assignee: Fresenious Medical Care Deutschland GmbH, Bad Homburg (DE)

( * ) Notice: Subject to any disclaimer, the term of this patent is extended or adjusted under 35 U.S.C. 154(b) by 356 days.

(21) Appl. No.: 10/856,087

(22) Filed: May 28, 2004

(65) Prior Publication Data

US 2005/0015040 A1    Jan. 20, 2005

(30) Foreign Application Priority Data

May 30, 2003   (DE) ............................... 103 24 668

(51) Int. Cl.
- A61M 37/00 (2006.01)
- A61N 1/30 (2006.01)
- A61M 31/00 (2006.01)
- A61M 1/00 (2006.01)
- A61B 5/00 (2006.01)

(52) U.S. Cl. .................... 604/4.01; 604/5.01; 604/6.08; 604/6.09; 604/6.11; 604/6.16; 604/21; 604/93.01; 422/44; 422/48; 600/310; 600/315

(58) Field of Classification Search ............. 604/19–21, 604/4.01, 5.01, 5.04, 6.08; 606/3; 607/80, 607/88, 87, 104; 210/600, 634, 645, 649
See application file for complete search history.

(56) References Cited

U.S. PATENT DOCUMENTS 4,350,156 A * 9/1982 Malchesky et al. ......... 604/6.04

(Continued)

FOREIGN PATENT DOCUMENTS

DE        40 26 022        2/1992

(Continued)

OTHER PUBLICATIONS http://en.wikipedia.org/wiki/Spectral_irradiance, accessed Jan. 25, 2007.*

(Continued)

*Primary Examiner*—Tatyana Zalukaeva
*Assistant Examiner*—Adam Marcetich
(74) *Attorney, Agent, or Firm*—Weingarten, Schurgin, Gagnebin & Lebovici LLP

(57) ABSTRACT

The invention concerns a device for the extracorporeal irradiation of a patient's (P) bodily fluid containing bilirubin, comprising a first (10) and a second (12) line which can be connected to the patient (P), an impermeable irradiation unit for bodily fluids (14) connected therewith and located between the first (10) and the second (12) lines, and at least one adjustable feed unit for bodily fluids (16) located in the first (10) and/or the second (12) line, wherein by means of at least one feed unit for bodily fluids (16) an adjustable flow of bodily fluid through the lines (10, 12) and the irradiation unit for bodily fluids (14) is achievable, in which the first line (10) is designed to continually circulate the bodily fluid drawn from the patient (P) and route it to the irradiation unit for bodily fluids (14), and the second line (12) is designed to continually circulate the irradiated bodily fluid to the patient (P), and in which the irradiation unit for bodily fluids (14) contains an radiation source for the emission of electromagnetic radiation with a wavelength greater than 430 nm, preferably in a spectrum from 450 to 530 nm. The invention furthermore concerns a corresponding method.

16 Claims, 5 Drawing Sheets

U.S. PATENT DOCUMENTS

| | | | | |
|---|---|---|---|---|
| 4,398,906 | A * | 8/1983 | Edelson | 604/6.08 |
| 4,444,190 | A * | 4/1984 | Mutzhas | 607/94 |
| 4,613,322 | A * | 9/1986 | Edelson | 604/6.08 |
| 4,737,140 | A * | 4/1988 | Lee et al. | 604/6.08 |
| 4,878,891 | A * | 11/1989 | Judy et al. | 604/5.02 |
| 5,270,192 | A * | 12/1993 | Li et al. | 435/174 |
| 5,304,113 | A * | 4/1994 | Sieber et al. | 604/6.08 |
| 5,628,727 | A * | 5/1997 | Hakky et al. | 604/6.08 |
| 5,744,042 | A * | 4/1998 | Stange et al. | 210/645 |
| 6,113,566 | A * | 9/2000 | Schleicher | 604/6.08 |
| 6,156,007 | A * | 12/2000 | Ash | 604/113 |
| 6,193,681 | B1 * | 2/2001 | Davidner et al. | 604/6.08 |
| 6,277,337 | B1 | 8/2001 | Goodrich, Jr. et al. | |
| 6,464,715 | B1 | 10/2002 | Gysens et al. | |
| 2005/0082225 | A1 * | 4/2005 | Kreymann | 210/639 |

FOREIGN PATENT DOCUMENTS

| | | |
|---|---|---|
| DE | 199 14 850 A1 | 10/2000 |
| JP | 63-275351 | 11/1988 |
| JP | 63 275351 | 11/1988 |
| WO | WO 0059551 | 10/2000 |
| WO | WO 01/94349 | 12/2001 |

OTHER PUBLICATIONS http://www.m-w.com/cgi-bin/dictionary?book=Dictionary&va=cuvette, accessed May 23, 2007.*

Online encyclopedia article "bilirubin" accessed Feb. 12, 2009. http://en.wikipedia.org/wiki/Bilirubin.*

Online encyclopedia article "Crigler-Najjar syndrome" accessed Jan. 20, 2010. http://en.wikipedia.org/wiki/Crigler-Najjar_syndrome.*

Chowdhury, J.R. et al., Hepatology, A Textbook of Liver Disease, (Chapter 9, pp. 233-269), publ. By D. Zakim and T.D. Boyer, Saunders, 2002.

Totsune, Kazuhito. "Innovation in Blood Purification for Hepatic Failure: Direct Photoirradiation of Plasma." Asaio Transactions, Harper and Row Publishers, Hagerstown, MD, US, Bd. 32, Nr. 1, Jul. 1, 1986. pp. 138-142.

* cited by examiner

DEVICE FOR EXTRACORPOREAL IRRADIATION OF A LIQUID CONTAINING BILIRUBIN, AND METHOD THEREFOR

This application claims priority to a German application No. 103 24 668.1 filed May 30, 2003.

DESCRIPTION

The invention presented concerns a device for extracorporeal irradiation of a liquid containing bilirubin in which bilirubin is converted into its water-soluble photo-isomers. The invention further covers a process for the reduction of the bilirubin level in a human being.

Bilirubin is derived from the catabolism of hemoglobin, and is formed in humans at a rate of approximately 300 mg per day. It is practically water-insoluble and cannot, therefore, be eliminated through the kidneys. Bilirubin binds to albumin (so-called "unconjugated" or "indirect" bilirubin) and is transported in this form in the blood. Bilirubin is converted in the liver into a water-soluble product (so-called "conjugated" or "direct" bilirubin) through a reaction with glucuronic acid. Conjugated bilirubin is excreted along with bile into the intestine, where it is further broken down by bacteria into an array of products called urobilinogens. The urobilinogens are eliminated in the stool and, after partial resorption from the intestines, through the kidneys.

Increases in bilirubin levels result from excessive erythrocyte decomposition, liver dysfunction or impaired hepatic excretion of bile. When bilirubin levels exceed glucuronidation and the subsequent excretion into bile, the result is hyperbilirubinemia, in which nonconjugated bilirubin (i.e. that bound to albumin) is elevated in plasma. Bilirubin concentrates in the phospholipid membranes of cells and, in sufficiently high concentrations, can pass through the blood-brain barrier (kernicterus). An increased risk of neurotoxic effects exists at a serum-bilirubin concentration of 20 mg/dl and up. The normal range of blood-bilirubin concentration in adults and children is less than 1 mg/dl. In patients with Crigler-Najjar syndrome type 1, the range is between 20 to 50 mg/dl.

Photochemical treatment (phototherapy) can convert bilirubin into polar, more hydrophilic derivatives. Bilirubin normally exists as Z,Z-bilirubin (4Z,15Z-bilirubin). Two photochemical mechanisms are of significance in the conversion of bilirubin in phototherapy:

1.) Configurational change to 4E,15Z-bilirubin and to 4Z,15E-bilirubin;
2.) Structural change to 4E,15Z- and 4Z,15E-cyclobilirubin.

Cyclobilirubin is stable, while modification to other forms of bilirubin produces unstable products which can reconvert to Z,Z-bilirubin. Additional reactions, such as photo-oxidation to biliverdin and photoaddition in albumin-bound bilirubin, also occur with low frequency (cf. S. Yasuda et al., Pediatr. Int. 43:270-275, 2001).

The ratio of E,Z-bilirubin to Z,Z-bilirubin increases with rising light intensity until it reaches a plateau (photoequilibrium) at a ratio of about 0.3 at approximately 3 $\mu W/(cm^2 \, nm)$. The conversion to cyclobilirubin increases linearly with rising light intensity without reaching a photoequilibrium (an equilibrium point) (cf. S. Yasuda et al., Pediatr. Int. 43:270-275, 2001, FIG. 3 and FIG. 4). Photoisomerization occurs during irradiation by light with a spectrum of 450 to 530 nm.

Z,Z-bilirubin is practically water-insoluble because it forms intramolecular hydrogen bonds. In contrast, the photoisomers are water-soluble, as the intramolecular hydrogen bonds characteristic of Z,Z-bilirubin have been broken at a minimum of one site. Cyclobilirubin is, therefore, very polar and more water-soluble than Z,Z-bilirubin. The photoisomers may be extracted from chloroform with water, whereby such extraction may be improved using increased pH (cf. P. Mannito et al., Pediatr. Res. 18: 378-381, 1984). The photoisomers can be eliminated through bile/intestine in unconjugated form. The concentration of cyclobilirubin found in urine during phototherapy ranges from 0.5 to 2.5 mg/dl; the concentration in bile is twice as high. The concentration of native Z,Z-bilirubin in urine is practically not elevated (<0.2 mg/dl) compared to its normal concentration.

In neonates one sees an elevated bilirubin level in blood (jaundice) relatively often, as much hemoglobin is catabolized during the prenatal adjustment of a very high hematocrit and the liver is not yet functioning effectively. An established procedure for the treatment of jaundice in neonates is the irradiation of skin with blue-to-green light. In this procedure bilirubin is converted via photoisomerzation into a water-soluble form which can be eliminated through the intestines and kidneys. Depending on the age of the neonate, the serum bilirubin threshold at which phototherapy should be initiated ranges from 15 to 20 mg/dl. Beyond the neonate stage, phototherapy is instituted in patients with Crigler-Najjar syndrome. Such patients have a congenital defect in the enzyme UDP-glucuronyltransferase, which converts bilirubin into a water-soluble form in the liver through conjugation with glucuronic acid. Phototherapy becomes increasingly ineffective, however, at the beginning of puberty. The increase in skin thickness and pigmentation, as well as the adversely increasing ratio of body surface area to volume, restricts the use of phototherapy in adult patients (cf. J. R. Chowdhury et al., Hepatology, published by D. Zakim, T D Boyer Saunders, 2002)

The objective forming the basis of the present invention is to provide a novel device for the extracorporeal irradiation of a liquid containing bilirubin in order to convert bilirubin into its photoisomers. A further objective of the invention is to specify a corresponding method.

This objective is solved pursuant to the invention by the device described in claim 1 and by the method in claim 10. Preferred embodiments are the subject of the dependent claims.

Pursuant to the invention, the device comprises a first and a second line which can be connected to the patient, an irradiation unit for bodily fluids located between the first and the second lines, and at least one adjustable feed unit for bodily fluids located in the first and/or the second line. An adjustable flow of bodily fluid in the device, in which the first line is designed to continually circulate the bodily fluid drawn from the patient and route it to the irradiation unit for bodily fluids, and the second line is designed to continually circulate the irradiated bodily fluid to the patient, is maintained by the feed unit.

One patient-connectable line can be directly connected to the patient. Alternatively, optional lines can be provided to maintain fluid contact between the patient and the first or second line.

The irradiation unit for bodily or other fluids features has, at a minimum, a partially translucent flow reservoir and an radiation source, preferably adjacent to the reservoir. The radiation source emits electromagnetic radiation preferably with a wavelength greater than 430 nm and more preferably in the spectrum from 450 to 530 nm. The irradiation intensity should be greater than 4 $\mu W/(cm^2 \, nm)$. The irradiation intensity of phototherapy is frequently specified as irradiance per bandwidth. In this way the measured irradiance is divided by the spectral bandwidth of the sensor. The bandwidth of phototherapy sensors is adjusted to the spectral range in which photoreactions take place, i.e. in the present invention, between 430 and 530 nm. Irradiation doses of less than 4 $\mu W/(cm^2\, nm)$ are not effective. The partially translucent flow reservoir can be, for example, a flow cuvette. The minimum specifications for the flow reservoir are good translucence in the spectrum from 400 to 530 nm and a large enough capacity that the fluid has a known duration in the cuvette, during which the photochemical reactions can take place.

The irradiation unit for bodily or other fluids has an adjustable fluid feed rate, and can produce an adjustable flow of bodily or other fluids through the device. The flow rate is in the range of 100 to 500 ml/min. In liver support therapy this rate is preferably 300 ml/min. The bodily fluid feed unit can be, for example, a pump.

Bilirubin is, in fact, converted into its water-soluble photoisomers by the aforementioned device; however, these isomers are not eliminated by the device. This assumes that the patient possesses sufficient kidney function to eliminate the photoisomers via the kidneys, similar to the treatment of neonates.

The device described in the invention can, in an additional embodiment, feature a photoisomer-removal unit for the removal of the photoisomer products of bilirubin. Thus the irradiated bodily fluid can be returned to the patient without the photoisomerization products of bilirubin. This device can be designed as an adsorber, a dialyzer and or a hemofilter. The efficiency of bilirubin removal can be sharply increased with the help of adsorbers, as the binding constants of Z,E-bilirubin and cyclobilirubin to albumin are clearly less than the binding constant of bilirubin to albumin.

In a further preferred embodiment the device features a filter—in particular, a plasma filter—with an unfiltered and a filtered side. The unfiltered side is separated from the filtered side by at least one filter material, e.g. a filter membrane. In this case, a fluid feed inlet to the unfiltered side is connected to a third patient-connectable line, a fluid discharge outlet from the unfiltered side is connected to a fourth patient-connectable line, a fluid discharge outlet from the filtered side is connected to the first line, and a fluid feed inlet to the filtered side is connected to the second line. In this manner, the first line may be connected to the patient over the third line, and the second line over the fourth line. The plasma filter preferably has a pressure gradient, so that filtration takes place in the forward section of the filter (fluid transfer from the unfiltered to the filtered side) and reverse filtration takes place in the rear section of the filter (fluid transfer from the filtered to the unfiltered side), i.e., the irradiated fluid is returned again to the patient.

The filter can retain cellular components of blood; however, albumin, albumin-bound bilirubin and additional small-molecule substances will pass through. Because of this, the albumin-bilirubin complex arrives in the first line, is irradiated in the bodily-fluid irradiation device, and the resulting photoisomers are subsequently returned to the patient via the second or fourth line. Irradiation can take place on the side with filtrate which contains plasma, as well as on the side with enriched fluid. There is an advantage to irradiating the side with filtrate which contains plasma only: light is not weakened by absorption by hemoglobin, as it would be on the other side. As an alternative to a plasma filter, a cell separator for separation of blood into plasma and cellular components can be built in. The cell separator can be a centrifuge, for example.

The device pursuant to this invention can also feature an adsorber in front of or after the irradiation unit for bodily fluids. This adsorber can be, for example, an anion-exchanger or a non-specific adsorber. While the anion-exchanger binds bilirubin, bile acid and other ions, a non-specific adsorber, such as a neutral resin, can retain other albumin-bound toxins.

An additional device pursuant to this invention is a ducting system which comprises a first and a second line which can be connected to the patient, as well as an impermeable flow reservoir located between the first and second lines. The flow reservoir is for electromagnetic radiation with wavelengths greater than 430 nm and preferably in the spectrum from 450 to 530 nm. It is at least partially translucent. In addition, it has a large enough capacity that the fluid has a known duration in the flow reservoir, during which the photochemical conversion of bilirubin can take place. This ducting system can preferably be used as a disposable for the device pursuant to this invention.

The device pursuant to this invention can be used effectively in the treatment of patients with liver failure who still have sufficient kidney function. The photoisomers of bilirubin can be eliminated through the kidneys, as they are in the treatment of neonates. A combination therapy with an artificial liver system would be advantageous. The function of the enzyme UDP-glucuronyltransferase would then be largely replaced by the irradiation unit for bodily fluids.

Furthermore, a method for the reduction of bilirubin levels in individual patients is revealed, in which a bodily fluid containing bilirubin is drawn from the patient and exposed to extracorporeal irradiation, whereby the bilirubin contained in the bodily fluid is converted into photoisomerization products with water-solubility greater than that of bilirubin, and the irradiated bodily fluid containing the created photoisomerization products is returned to the patient.

The method can be executed by means of the embodiments described above pursuant to the invention.

The method is intended for the treatment of elevated bilirubin levels in all forms of liver failure. The method pursuant to the invention is simple to implement, cost-effective, and non-critical with respect to the safety of the application. The method may be combined simply with all existing methods of liver support therapy, such as albumin dialysis or bilirubin adsorber. As the photoisomers have a smaller binding constant than bilirubin to albumin, a clear increase in the effectiveness of bilirubin removal is possible.

The invention is described below with reference to the accompanying diagrams. Exhibits:

FIG. 1 a schematic block diagram of a preferred embodiment of a device pursuant to the invention with the first line (10), second line (12), irradiation unit for bodily fluids (14) and feed unit for bodily fluids (16);

FIG. 2 a schematic block diagram of an additional preferred embodiment of a device pursuant to the invention with the first line (10), second line (12), irradiation unit for bodily fluids (14), feed unit for bodily fluids (16) and photoisomer-removal unit (18);

FIG. 3 a schematic block diagram of an additional preferred embodiment of a device pursuant to the invention with the first line (10), second line (12), irradiation unit for bodily fluids (14), feed unit for bodily fluids (16), photoisomer-removal unit (18), filter/cell separator (20), third line (24), fourth line (27), fluid feed inlet to the unfiltered side (22), fluid discharge outlet from the unfiltered side (26), fluid discharge outlet from the filtered side (28), and fluid feed inlet to the filtered side (29);

FIG. 4 a schematic block diagram of an additional preferred embodiment of a device pursuant to the invention with the first line (10), second line (12), irradiation unit for bodily fluids (14), feed unit for bodily fluids (16), photoisomer-removal unit (18), filter/cell separator (20), third line (24), fourth line (27), fluid feed inlet to the unfiltered side (22), fluid discharge outlet from the unfiltered side (26), fluid discharge outlet from the filtered side (28), fluid feed inlet to the filtered side (29) and adsorber (30);

FIG. 5 a schematic block diagram of an additional preferred embodiment of a device pursuant to the invention with the first line (10), second line (12), irradiation unit for bodily fluids (14), feed unit for bodily fluids (16), photoisomer-removal unit (18), filter/cell separator (20), third line (24), fourth line (27), fluid feed inlet to the unfiltered side (22), fluid discharge outlet from the unfiltered side (26), fluid discharge outlet from the filtered side (28), and fluid feed inlet to the filtered side (29) and adsorber (30);

FIG. 6 the photoisomerization of 4Z, 15Z-bilirubin to 4E, 15Z-bilirubin and 4Z, 15E-bilirubin;

FIG. 7 the photoisomerization of 4Z, 15E-bilirubin to cyclobilirubin;

FIG. 8 a schematic drawing of the experimental set-up for bilirubin phototherapy in the hemofiltration mode (Example 1);

FIG. 9 the concentration curve of cyclobilirubin in the filtrate in Example 1 during irradiation.

The first embodiment of a device pursuant to the invention is shown in FIG. 1. It shows the first line (10) with a first and a second end. The first end of line 10 may be connected to the patient (P), and the second end is connected to the irradiation unit for bodily fluids (14). The second line (12) also has a first and a second end. The first end is connected to the irradiation unit for bodily fluids (14), and the second end may be connected to the patient (P). The flow rate through lines 10 and 12, i.e. the pumped fluid volume per unit of time, is controlled by a bodily fluid feed mechanism (16). Bodily fluid, e.g. blood, can be drawn continuously from Patient (P) through line 10 and irradiated in the irradiation unit for bodily fluids (14). The irradiated blood is circulated back to the patient (P) through the second line (12). This device has the advantage that no foreign substances, such as adsorber material, interfere with patient blood/plasma during removal of bilirubin. Thus the biocompatibility of the method is very high and the danger of complement activation, for example, is significantly reduced. Because the device can be connected directly to the patient, one sees a reduction in treatment time and the simplification of various procedures (e.g. blood draw, irradiation, etc.), enabling a very rapid removal of bilirubin from patient circulation. In this embodiment of the invention, sufficient patient kidney function and perhaps residual function of the liver are admittedly critical. This embodiment is, however, ideal for patients with Crigler-Najjar syndrome, for whom conventional phototherapy is limited due to patient age.

FIG. 2 shows a device based upon that in FIG. 1, with the addition of a unit for the removal of photoisomers (18) following the bodily-fluid irradiation unit (14) in the second line (12). This photoisomer-removal unit can be built as an adsorber, hemofilter and/or dialyzer. If the photoisomer-removal unit (18) is a dialyzer or hemofilter, it has additional inlet and discharge lines, e.g. dialysis lines or a fluid substitute feed. One such design is particularly beneficial to patients (P) with insufficient kidney function, as the photoisomers are absorbed in the photoisomer-removal unit and do not need to be eliminated through the kidneys.

FIG. 3 shows an additional embodiment of the device in which the identical parts are labeled with the same numbers as in FIG. 1. The third line (24) has a first and a second end. The first end may be connected to patient (P) and the second end is connected to the fluid feed inlet (22) of the unfiltered side of a filter (20). The filter (20) has a filtered side next to the unfiltered side, each separated from the other by, at a minimum, filter material. The fourth line (27) has a first and a second end. The first end is connected to the fluid discharge outlet (26) of the unfiltered side of a filter (20) and the second end may be connected to the patient (P). The bodily fluid, which enters through the fluid feed inlet (22) to the unfiltered side, can partially leave through the fluid discharge outlet (28) of the filtered side. The filtered bodily fluid is then fed by the first line (10) to the irradiation unit for bodily fluids (14), and can subsequently flow via the second line (12) optionally through a photoisomer-removal unit (18). The filtered, irradiated bodily fluid again enters the filter (20) via the fluid feed inlet (29) of the filtered side and exits via the fluid discharge outlet (26) of the unfiltered side into the fourth line. The unfiltered bodily fluid and the filtered, irradiated and optionally photoisomer-free bodily fluid converge again in the fourth line (27). When dealing with a bodily fluid such as blood, only the blood plasma is irradiated, as all cellular components of blood are isolated by the filter (20). A cell separator (e.g. a centrifuge) can be used as an alternative to the filter (20) to separate blood into plasma and cellular components.

An advantage of the device described in this invention is the greater effectiveness of limited irradiation vis-à-vis whole-blood irradiation. As hemoglobin also demonstrates absorption of light in this spectrum, one can avoid unwanted reactions which may arise from high light-intensity, such as warming or photoreactions.

The fluid flow rate on the filtered side can be considerably greater than that on the unfiltered side—i.e., recirculation dominates on the filtered side—through the use of an adjustable fluid feed unit (16) in the first (10) or second (12) line and an adjustable fluid feed unit in the third (24) and/or the fourth (27) line. The photoisomer-removal unit is better utilized in this situation, as the filtered fluid flows through the unit multiple times.

If the filter (20) is a dialyzer, an albumin solution exists on the permeate side of the dialyzer. Bilirubin then diffuses out of the bodily fluid without albumin to the permeate side of the dialyzer. There it is converted by irradiation into its photoisomers and removed by the photoisomer-removal unit (18), i.e. the photoisomers do not return to the patient (P). The removal of bilirubin with the help of the photoisomer-removal unit (18) is markedly more effective, as the binding constants of Z,E-bilirubin and cyclobilirubin to albumin are considerably smaller than the binding constant of Z,Z-bilirubin to albumin.

FIG. 4 shows an additional preferred embodiment which is similar to and based upon that in FIG. 3. The embodiment per FIG. 4 has an adsorber (30) located in the first line (10) prior to the irradiation unit for bodily fluids (14), and the optional photoisomer-removal unit (18) is located in the fourth line (27) only after the combination of unfiltered bodily fluid and filtered, irradiated bodily fluid. Other albumin toxins can be bound in the device through the combination of the original device specified in the invention with an adsorber, so that in one step both bilirubin and unwanted toxins can be removed from the blood.

FIG. 5 shows an additional preferred embodiment which is similar to and based upon that in FIG. 3. In the embodiment per FIG. 5, the irradiation unit for bodily fluids (14) is located in the fourth line (27) after the combination of unfiltered bodily fluid and filtered fluid treated by the adsorber. In addition, the optional photoisomer-removal unit (18) is located in the fourth line (27) after the irradiation unit for bodily fluids (14).

Figure 1:
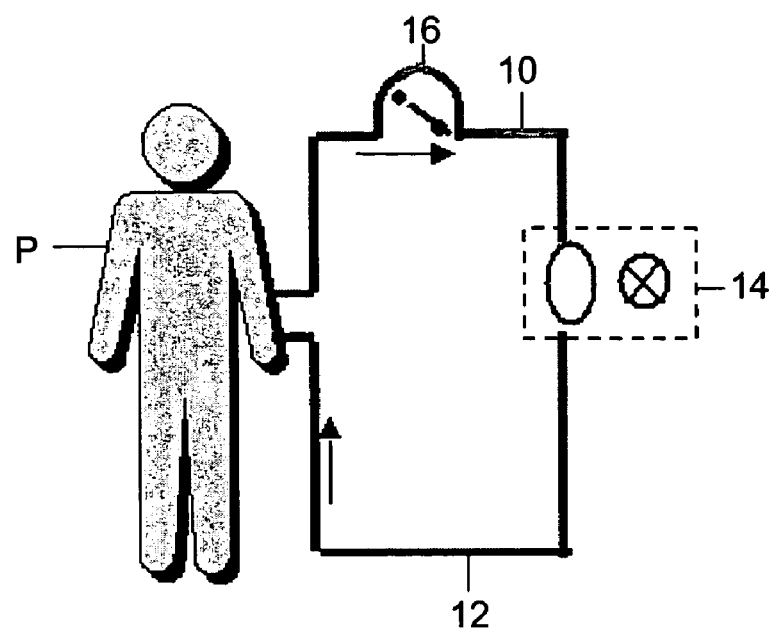
Figure 2:
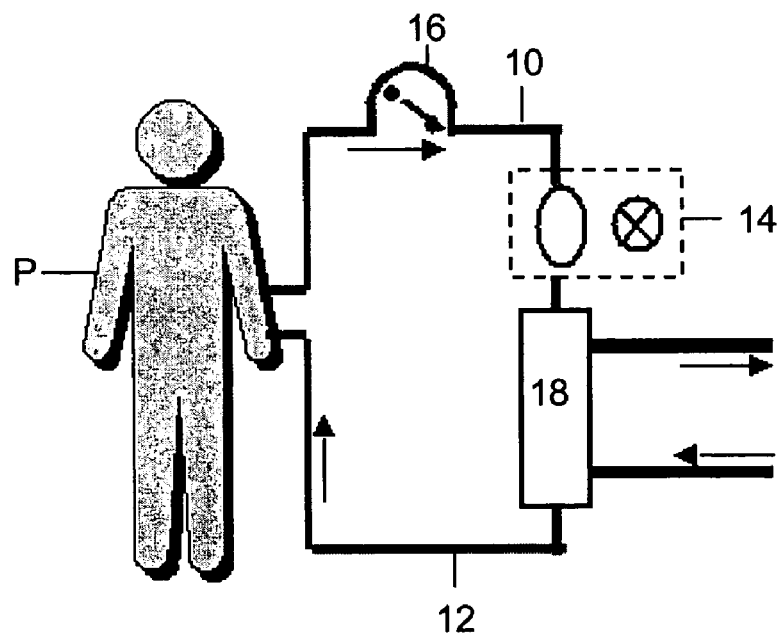
Figure 3:
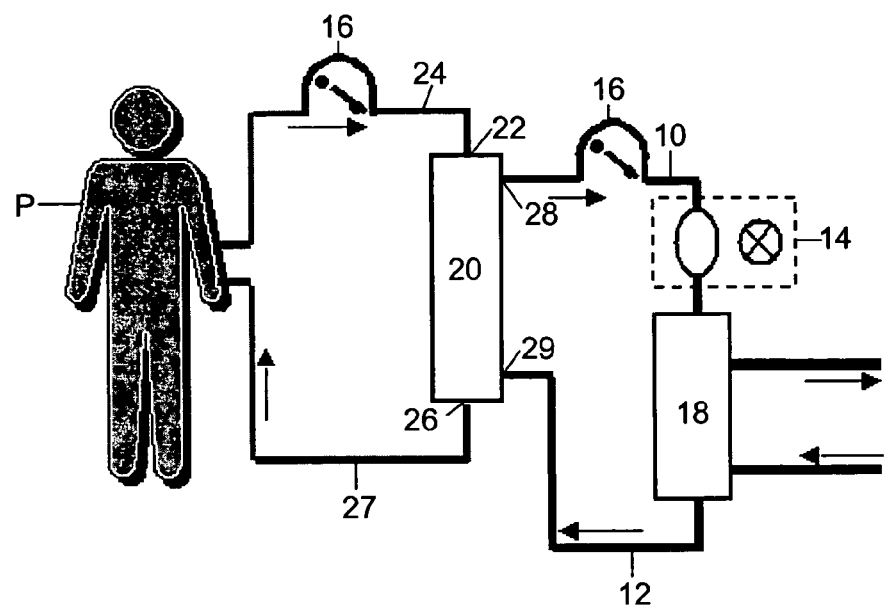
Figure 4:
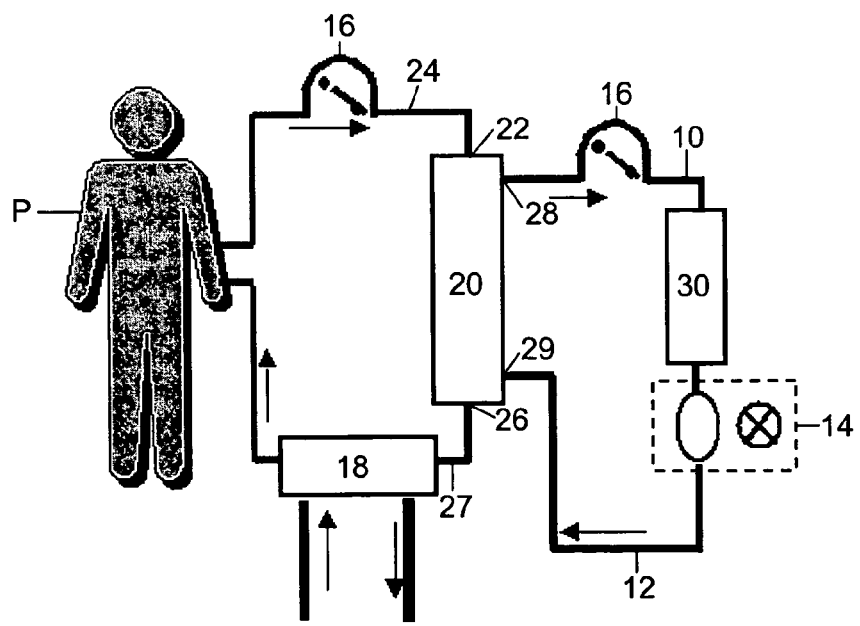
Figure 5:
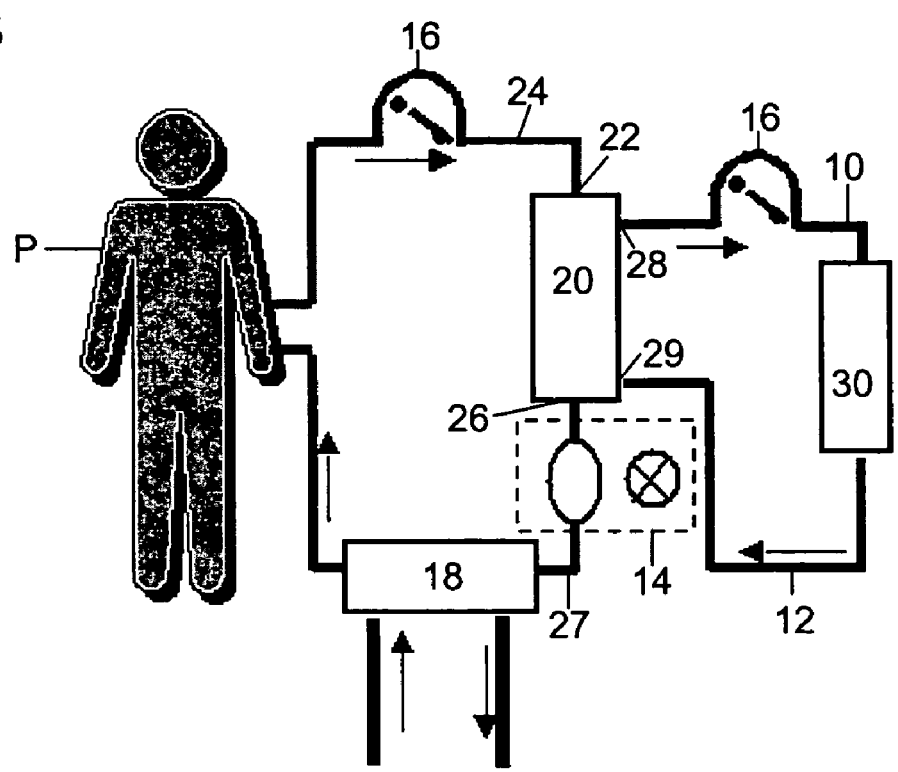
Figure 6:
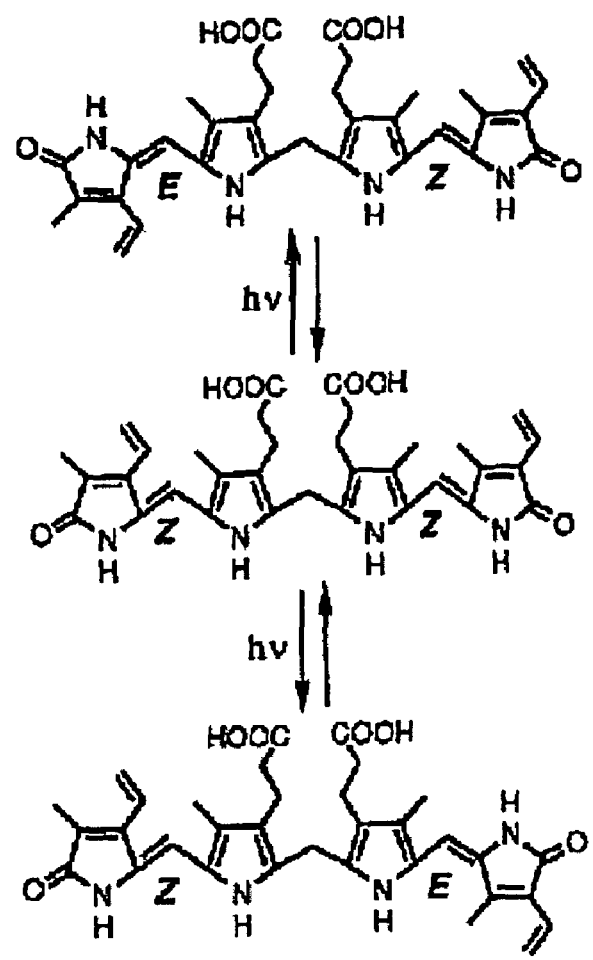
FIG. 6 shows the photoisomerization of 4Z,15Z-bilirubin to 4E,15Z-bilirubin and 4Z,15E-bilirubin as recognized in the state of the art.
Figure 7:
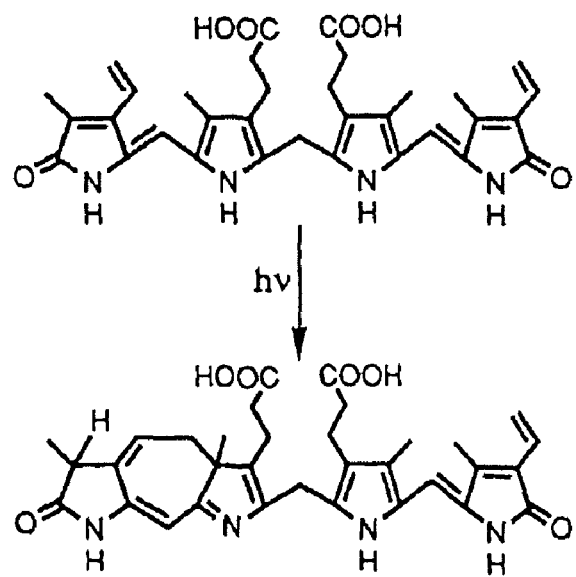
FIG. 7 shows the photoisomerization of 4Z,15E-bilirubin to cyclobilirubin as recognized in the state of the art.
Figure 8:
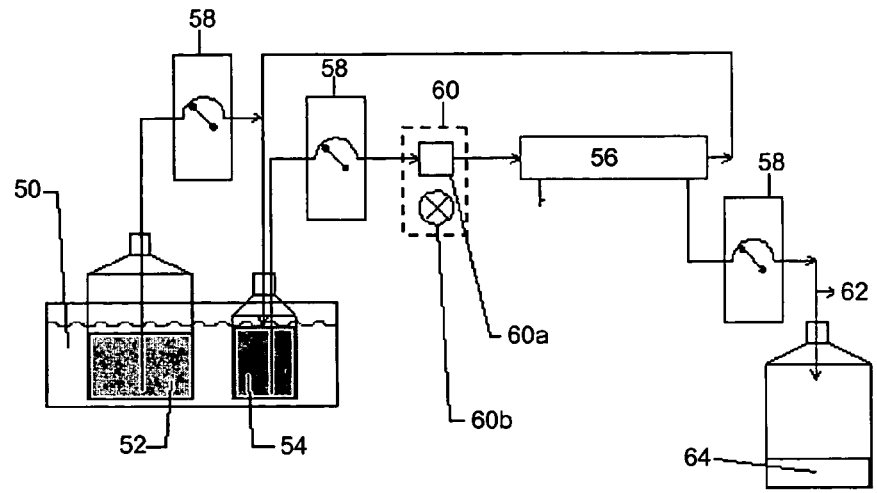

FIG. 8 shows an in vitro experimental design of a device pursuant to the invention with a water bath (50) which is kept preferably at 37° C. The water bath (50) contains a bilirubin/HSA solution (54) and a buffer solution (52). A continuous flow through the lines, the irradiation unit for fluids (60) and the hemofilter (56) is achieved by the pump (58). The direction of fluid flow is indicated by the arrows. The irradiation unit for fluids consists of an radiation source (60b) and an arterial bubble chamber as a cuvette (60a). The volume of bilirubin/HSA solution remains roughly constant for the duration of the experiment, as the fluid volume, which is pumped out of the rear section (related to the direction of flow) of the hemofilter (56) by a pump (58), is replaced by a buffer solution (52) delivered by a pump (58). The filtrate (64) pumped out of the hemofilter (56) can then be measured.

In conclusion, it must be noted that, although the invention was described on the basis of the embodiments above, specific characteristics and elements revealed in this connection can also find application in other embodiments and can be integrated into new embodiments.

EXAMPLE 1

250 ml of a bilirubin/HSA solution (bilirubin: Sigma, Prod. No. B4126; HSA: Human serum albumin, Biotest Pharma GmbH, Dreieich) with a bilirubin concentration of 15 mg/100 ml and an albumin concentration of 30 g/l were recirculated as shown in FIG. 8 at a flow of 100 ml/min through an arterial bubble chamber (Schlauchset FA104, Fresenius), part of a fluid-irradiation unit, and through an in-line hemofilter (F3, Fresenius). In addition, filtrate was pumped out of the rear filtrate adapter of the hemofilter. In order that the volume of bilirubin/HSA solution remained roughly constant for the duration of the experiment, hydrogen-carbonate-buffer solution (produced with the concentrations BC-F 8.4% and SK-F 003) was substituted with an equal flow in the venous side of the bilirubin/HSA circulation.

In order to remove the water-soluble, non-physiological isomers of bilirubin IIIα and XIIIα, which are contained in the Sigma product at 6%, the first 50 minutes of the experimented proceeded without irradiation. Following this, irradiation proceeded for 160 minutes with a cold-light source (KL 1500, Schott) with an advanced long-pass filter which allowed light above 435 nm to pass through (Sperrfilter GG 435, AHF Analysentechnik, Tuebingen). The irradiance amounted to $E_{410-485}$=5.25 mW/cm$^2$ (70 µW/(cm$^2$ nm)). The concentration of cyclobilirubin in the filtrate was measured in the spectralphotometer at a wavelength of 440 nm in a cuvette of 10 cm irradiance.

Figure 9:
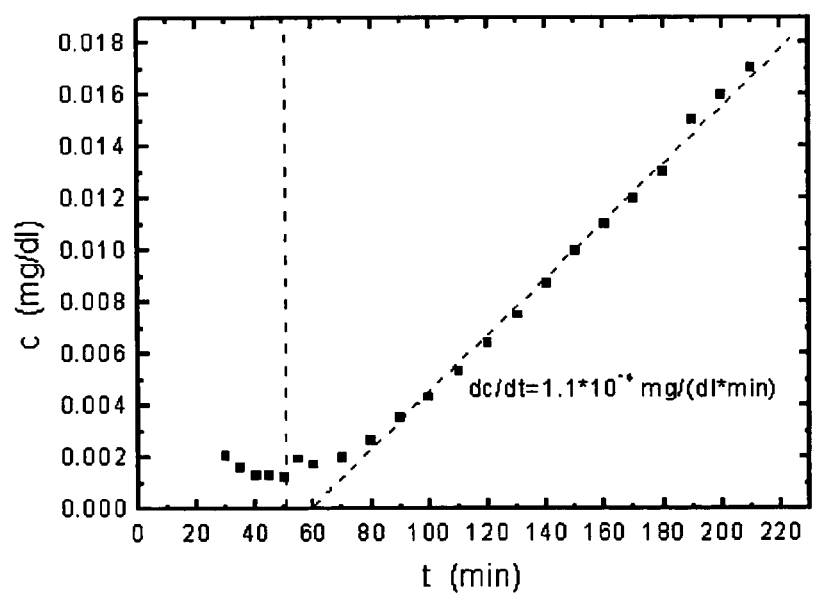

FIG. 9 shows the concentration curve of cyclobilirubin in the filtrate during the hemofiltration experiment. The measured extinction was calibrated with the published value of the extinction coefficient of cyclobilirubin (e=33000M$^{-1}$cm$^{-1}$) in the concentration.

The experiment shows the flushing-out of the non-physiological isomers of bilirubin during the first 50-minute sequence in the dark. After the radiation source is turned on, a clear increase in concentration of $1.1\times10^{-4}$ mg/100 ml per minute is seen. The concentration in the filter corresponds to the concentration of free (i.e. not bound to albumin) photoisomers in the bilirubin/HSA solution after the irradiation.

The experiment demonstrates that free photoisomers arise from the irradiation of albumin-bound bilirubin, and that these photoisomers can be removed by a hemofilter. Thus is the principle of extracorporeal bilirubin phototherapy demonstrated.

LEGEND

10 First line
12 Second line
14 Irradiation unit for bodily and other fluids
16 Feed unit for bodily and other fluids
18 Photoisomer-removal unit
20 Filter/cell separator/dialyzer/hemofilter
22 Fluid feed inlet of the filter/dialyzer/hemofilter on the unfiltered or the dialyzing side
24 Third line
26 Fluid discharge outlet of the filter/dialyzer/hemofilter on the unfiltered or the dialyzing side
27 Fourth line
28 Fluid discharge outlet of the filter on the filtered or permeate side
29 Fluid feed inlet of the filter/dialyzer/hemofilter on the filtered or permeate side
30 Adsorber

The invention claimed is:

1. Device for extracorporeal irradiation of a bodily fluid from a patient past the onset of puberty, said bodily fluid containing bilirubin, comprising a first and a second line which can be connected to the patient, an impermeable irradiation unit for bodily fluids connected therewith and located between the first and the second lines, and at least one adjustable feed unit for bodily fluids located in the first and/or the second line, wherein a feed unit for bodily fluids is configured to provide an adjustable flow of bodily fluid through the lines and the irradiation unit for bodily fluids in which the first line is configured to continually circulate the bodily fluid drawn from the patient and route it to the irradiation unit for bodily fluids, and the second line is configured to continually circulate the irradiated bodily fluid to the patient, and in which the irradiation unit for bodily fluids contains a radiation source for the emission of electromagnetic radiation with a wavelength greater than 430 nm and an irradiation intensity of greater than 4 µW/(cm$^2$ nm) as applied directly to said bodily fluids in said irradiation unit, the device further comprising a plasma filter or cell separator with a cell-containing side and a cell-free side, wherein a fluid feed inlet to the cell-containing side is connected to a third patient-connectable line, a fluid discharge outlet from the cell-containing side is connected to a fourth patient-connectable line, a fluid discharge outlet from the cell-free side is connected to the first line, and a fluid feed inlet to the cell-free side is connected to the second line, said device configured to irradiate free and bound bilirubin obtained from said bodily fluid, and configured for use with a patient past the onset of puberty.

2. Device according to claim 1, in which a photoisomer-removal unit for the removal of water-soluble photoisomers of bilirubin is located in the second line.

3. Device according to claim 1, in which the irradiation unit for bodily fluids contains a partially translucent flow reservoir.

4. Device according to claim 3, in which the partially translucent flow reservoir is a flow cuvette.

5. Device according to claim 1, in which the photoisomer-removal unit is built as an adsorber, hemofilter and/or a dialyzer.

6. Device according to claim 1, in which the feed unit for bodily fluids is a pump.

7. Device according to claim 1, in which the bodily fluid is blood or blood plasma.

8. A system comprising a device according to claim 1 in combination with a bioartificial liver system.

9. The device according to claim 1, wherein said electromagnetic radiation has a wavelength in the spectrum from 450 to 530 nm.

10. Method for the reduction of bilirubin levels in a patient, comprising:
    drawing a bodily fluid containing bilirubin from a patient not treatable by phototherapy directed to the skin,
    processing said bodily fluid to produce a cell-free bodily fluid comprising free and bound bilirubin obtained from said bodily fluid and a cell-containing bodily fluid,
    exposing said cell-free bodily fluid to extracorporeal irradiation at an irradiation intensity greater than $4 \, \mu W/(cm^2 \, nm)$, whereby the bilirubin contained in the cell-free bodily fluid is converted into photoisomerization products with water-solubility greater than that of bilirubin, and
    returning the cell-containing bodily fluid and the irradiated cell-free bodily fluid containing the created photoisomerization products to the patient.

11. Method according to claim 10, whereby irradiation with electromagnetic radiation with wavelengths of at least 430 nm is conducted.

12. The method of claim 11, wherein said electromagnetic radiation has a wavelength in the spectrum from 450 to 530 nm.

13. The method of claim 10, wherein said patient has liver failure.

14. The method of claim 10, wherein the patient is past the onset of puberty.

15. The method of claim 10, wherein the patient is an adult.

16. The method of claim 10, wherein the patient has Crigler-Najjar Syndrome.

* * * * *

UNITED STATES PATENT AND TRADEMARK OFFICE
CERTIFICATE OF CORRECTION

| | | |
|---|---|---|
| PATENT NO. | : 7,846,121 B2 | Page 1 of 1 |
| APPLICATION NO. | : 10/856087 | |
| DATED | : December 7, 2010 | |
| INVENTOR(S) | : Andreas Wuepper | |

It is certified that error appears in the above-identified patent and that said Letters Patent is hereby corrected as shown below:

Title Page;

Item (75) Inventor: "Bad Homberg (DE)" should read --Büttelborn (DE)--; and

Item (73) Assignee: "Fresenious Medical Care Deutschland GmbH" should read --Fresenius Medical Care Deutschland GmbH--.

Signed and Sealed this
Third Day of May, 2011

David J. Kappos
*Director of the United States Patent and Trademark Office*